United States Patent [19]

Bálint et al.

[11] Patent Number: 4,584,135

[45] Date of Patent: Apr. 22, 1986

[54] PROCESS FOR THE PREPARATION OF AN OXYTETRACYCLINE-CALCIUM SILICATE COMPLEX SALT FROM FERMENTATION BROTH

[75] Inventors: János Bálint; László Cséke; Ferenc Fábián; Lajós Kün; Miklós Szarvas, all of Debrecen, Hungary

[73] Assignee: Biogal Gyogyszergyar, Debrecen, Hungary

[21] Appl. No.: 537,293

[22] Filed: Sep. 29, 1983

[51] Int. Cl.$^4$ ............................................. C07C 103/26
[52] U.S. Cl. ................................ 260/351.6; 260/351.2
[58] Field of Search ........................... 260/351.6, 351.2

[56] References Cited

U.S. PATENT DOCUMENTS

| | | | |
|---|---|---|---|
| 2,649,480 | 8/1953 | Regna et al. | 260/351.6 |
| 2,740,816 | 4/1956 | Starbird et al. | 260/351.6 |
| 2,831,878 | 4/1958 | Esminger et al. | 260/351.6 |
| 2,847,471 | 8/1958 | Vandeputte et al. | 260/351.6 |
| 2,915,555 | 12/1959 | Solomons, III | 260/351.6 |

FOREIGN PATENT DOCUMENTS

| | | | |
|---|---|---|---|
| 632331 | 5/1963 | Belgium | 260/351.6 |
| 143609 | 8/1957 | Hungary | 260/351.6 |
| 172330 | 5/1979 | Hungary | 260/351.6 |
| 718020 | 4/1951 | United Kingdom | 260/351.6 |

OTHER PUBLICATIONS

Merck Index 10th Edition, Compound 1680.
Blue Circle Ind., *Chemical Abstracts*, vol. 91, No. 62246x, 4/25/79.
Koide et al., *Chemical Abstracts*, vol. 89, No. 152100h, 7/20/78.
Goto et al., *Chemical Abstracts*, vol. 93, No. 137807h, 1980.
Merck Index 10th Edition Compounds 5509 and 9964.

*Primary Examiner*—Glennon H. Hollrah
*Assistant Examiner*—Raymond Covington
*Attorney, Agent, or Firm*—Karl F. Ross; Herbert Dubno

[57] ABSTRACT

The invention relates to a process for the preparation of an oxytetracycline-calcium silicate complex salt from fermentation broth.

By the process according to the invention the valuable antibiotic oxytetracycline may be separated from the fermentation broth in an easy manner. The complex obtained according to (a) contains up to 50% of antibiotic and is suitable for the processing in the pharmaceutical industry while the product according to (b) contains 10 to 20% of antibiotic and may be used as fodder additive directly.

21 Claims, 1 Drawing Figure

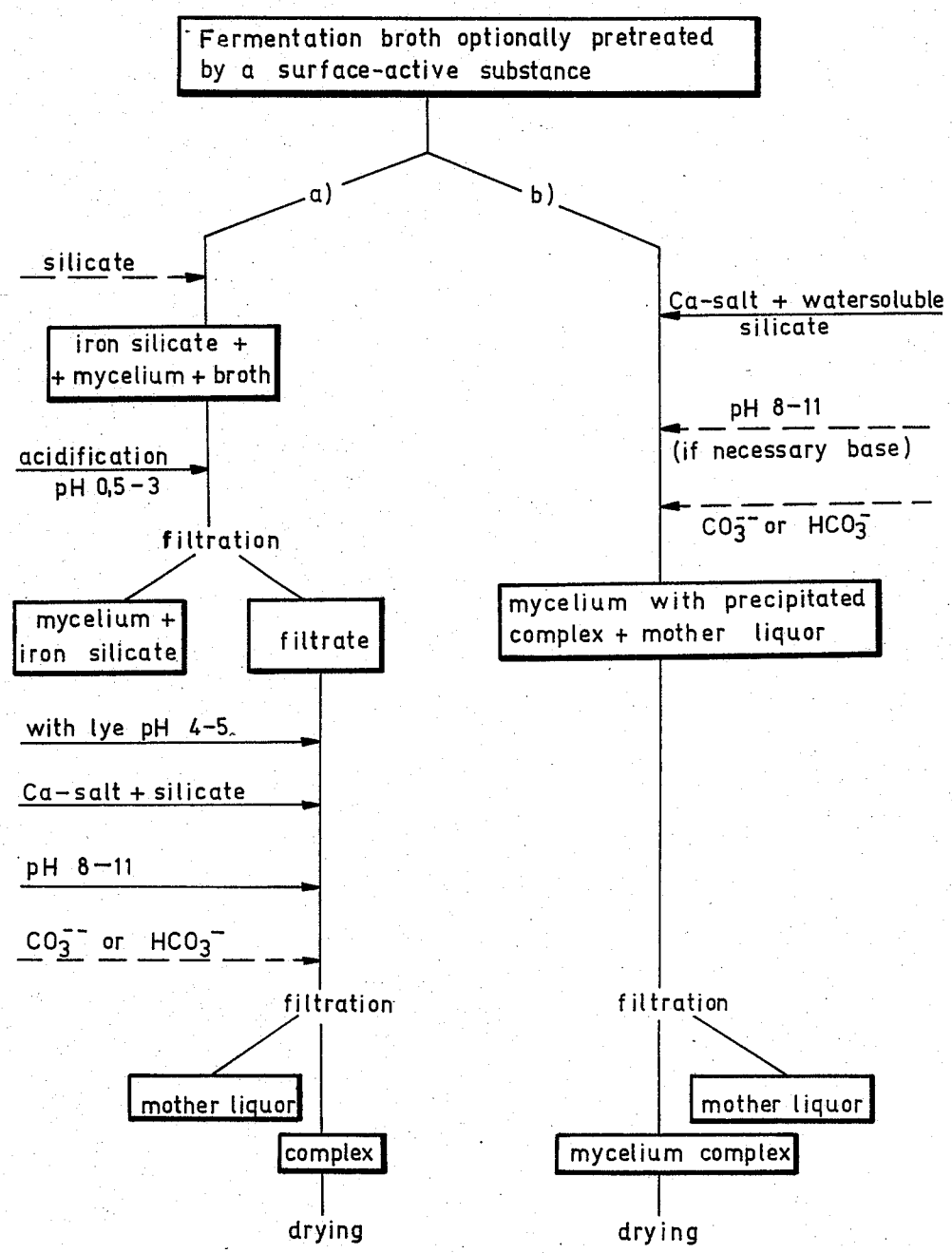

PROCESS FOR THE PREPARATION OF AN OXYTETRACYCLINE-CALCIUM SILICATE COMPLEX SALT FROM FERMENTATION BROTH

The invention relates to a simple, industrial process for the preparation of an oxytetracycline-calciumsilicate complex salt from a fermentation broth.

The oxytetracycline (OTC) is an antibiotic inhibiting the protein synthesis and the replication mechanism of numerous microorganisms which are used for the treatment of numerous diseases caused by pathogen microorganisms as well as owing to its weight-gain promoting and disease-preventing activity in agriculture as a fodder additive. In large scale production OTC is produced by aerobic fermantation of streptomyces rimosus in a submerged culture followed by the isolation of the antibiotic from the raw fermentation broth and by the purification of the raw material.

Numerous processes for the isolation and purification of the OTC are known. E.g. OTC may be extracted from an alkaline solution with butylalcohol (U.S. Pat. No. 2,516,080). Furthermore it may be attached to an ion exchange resin (U.S. Pat. No. 2,658,078), precipitated by barium, calcium or magnesium ions (J. Am. Chem. Soc. 73 (1951) 4211; British patent specificatin No. 718,028), by quaternary ammonium salts (U.S. Pat. No. 2,873,276) or by arylazosulfonic acids (U.S. Pat. No. 2,649,480). The cited processes have different disadvantages, e.g. the use of expensive apparatus, such as extractors, ion exchange columns or expensive chemicals (ion exchanger, quaternary ammonium salts, arylazosulfonic acids) or very toxic compounds (barium salts).

It seems that the process according to Belgian patent specification No. 632,331 can be carried out essentially simpler and easier; the OTC is precipitated in the presence of calcium ions by carbonate or hydrogen carbonate ions. However, the process proved to be hardly reproducible by us; the yield is not indicated in the cited publication.

A similar process (Hungarian patent specification No. 173,703) results in a maximum yield of 55%. According to Hungarian patent specificatin No. 172,330 the OTC is precipitated onto the mycelium with a yield of 85%. Thus the pure active agent content of the product is naturally very low (about 13%). This fact is rather disadvatageous both for the preparation and the further purification since one has to work with very high volumes.

The large scale production, isolation and purification of the OTC is very difficult because of the iron content of the fermentation broth. Iron gets into the fermentation broth with the components of the nutrient medium and from the wall of the iron fermenters and catalyzes the decomposition of the OTC as oxidizing agent, that is it reduces the quantity of the already synthesized active agent (Hungarian Patent specification No. 143,609) and spoils the yield of the purification steps (British patent specification No. 718,020). The iron content disadvantageously influences the color and the stability of the pure product, too; it is known that the di- and trivalent metals form stable inner complexes with the OTC (J. Am. Chem. Soc. 73 (1951), 4211) which are not easy to decompose. One possibility to maintain the iron content of the fermentation broth on a low level during the fermentation is the use of fermenters made of special steel. However, these apparatuses are too expensive, for this reason fermentors made of iron are mostly used everywhere in the fermentation industry.

The iron concentration of the OTC containing fermentation broth produced in iron fermenters is fairly high (about 30–60 gamma/ml, higher values are possible, too).

One tries to reduce the harmful effect of iron by converting it into soluble but not dissociating complexes with different methods. The best known complexing agent for this purpose is the ethylenediaminotetra-acetic-acid (EDTA). Another possibility is to reduce the trivalent iron e.g. by ascorbic acid, sodium-formaldehyde-sulfoxylate or sodium-dithionite to divalent iron because the divalent iron-OTC- complexes are fairly unstable and the divalent iron-ion does not catalyze the oxidation of the active agent. Finally, the iron can be precipitated e.g. by potassium-[hexacyanoferrate(II)] as insoluble iron (II, III)-[hexacyanoferrate(II)] (British patent specification No. 718,020). These processes have the disadvantage of using expensive reagents (EDTA, ascorbic acid) even in high quantities, but these cannot completely eliminate the harmful effect of iron. The reagent being most suitable for the precipitation of iron was potassium-[hexacyanoferrate(II)], but using it in the production means the possibility of forming hydrogen cyanide.

The object of the invention was to develop a process by means of which OTC can be produced more economically, with a higher yield than before and if desired in a higher degree of purity with a simple technology and simple apparatus.

The invention is based in the recognation that OTC forms an insoluble, stable, easily filterable complex salt with water-soluble silicates in the presence of calcium ions.

Accordingly the invention relates to a process for the preparation of an oxytetracycline-calciumsilicate-complex salt from the fermentation broth. According to the invention the fermentation broth (optionally pretreated with a surface-active substance)

(a) after an optional pretreatment with a water-soluble silicate is acidified to a pH-value of 0.5 to 3.0, then filtered off the mycelium—optionally using a filter aid—the pH-value of the filtrate is adjusted to 4–5 by a water-soluble lye and after the addition of a calcium salt or in the presence of calcium ions a water-soluble silicate and optionally a water-soluble carbonate or hydrogen carbonate is added, after longer stirring the formed oxytetracycline-calciumsilicate-complex salt is filtered off optionally in the presence of a filter aid, or (b) is mixed with a calcium salt and a water-soluble silicate, if necessary the pH-value is adjusted to 8-11 by a water-soluble lye, optionally a water-soluble lye, optionally a water-soluble carbonate or hydrogen-carbonate is added to the mixture and after a long stirring the oxytetracycline-calciumsilicate complex salt precipitated onto the mycelium is filtered off in the presence of a filter aid, and the oxytetracycline-calciumsilicate complex salt obtained according to paragraph (a) or (b) is dried at a temperature of 20° to 120° C.

According to variant (a) the mycelium is filtered off after the acidification and the calciumsilicate complex is formed in the pure filtrate. According to process variant (b) the complex is directly precipitated onto the mycelium. Variant (b) consists of fewer steps, however, this product can be used only as a fodder additive. According to variant (a) if desired an iron-free, very pure product can be obtained which can be further processed for pharmaceutical purposes.

The process is demonstrated in detail by means of a flow diagram.

Before the processing is started, the fermentation broth can optionally be pretreated with a surface-active substance. E.g. Sterogenol (cetylpyridiniumbromide) is suitable. The surface-active substance essentially destroys the cell walls of the microorganism (*Streptomyces rimosus*) and thus sets free the introcellularly bound OTC, too.

This process called plasmolysis takes place at a pH-value of 5.3 to 5.6 and a temperature of about 40° C. while 0.001 to 0.03% (related to the weight of the fermentation broth) is added until the complete dissolution of the cells. The fermentation broth treated with the above mentioned quantity of Sterogenole is free of cells under a microscope.

The plasmolysis is not necessary in every case. It is generally performed only if the fermentation broth is very thick and it is difficult to stir it, which is particularly the case if during the fermentation fats and oils are added in order to prevent foam formation. In the case of such fermentation broth the yield of OTC may be highly increased by treating it with a surface-active substance because the quantity included in the cells, too, which otherwise would be lost, is affected, too.

According to process variant (a) the fermentation broth is optionally pretreated by a water-soluble silicate. This step is carried out if an iron-free product shall be obtained. Related to its weight 0.1 to 3.0% preferably 1.5 to 2.0% of a water-soluble silicate, suitably soda water-glass, are added to the fermentation broth. Both iron (II) and iron (III) are precipitated by the silicate ions in form of the silicates thereof, and they are insoluble in weak bases and weak acids. The precipitated iron silicates are later separated by the filtration process together with the mycelium.

The acidification of the fermentation broth to a pH-value of 0.5 to 3.0 preferably to 1.0 to 2.0, is the following step. Organic and inorganic acids alike may be used for it. The use of phosphoric acid or acetic acid is not advisable because these acids catalyze the epimerisation of the OTC to the biologically ineffective 4-epimer. Hydrochloric acid attacks the active agent OTC too strongly. Oxalic acid and sulfuric acid proved to be the best ones. To use only oxalic acid is not economical. The best is to use their mixture, which consists of about 90% sulfuric acid and 10% oxalic acid. A mixture containing 11 percent by weight of sulfuric acid and 1.5 percent by weight of oxalic acid is used in a quantity of 30 to 120 ml, preferably 45 to 70 ml, related to 1 kg of the fermentation broth. Though in the course of the acidification a certain decompostion of the OTC takes place (J. Am. Chem. Soc. 75 5455 (1953), the losses can be kept under 6% by choosing the conditions appropriately.

Now the mycelium (if iron silicate is precipitated, this too) is separated from the acidic fermentation broth by filtration. If necessary a filteraid, such as perlite, can be used. The mycelium on the filter is once washed out with an acid of the said composition, the wash liquid is unified with the filtrate. In this way maximum 8% of the total active agent remains in the mycelium. This quantity could be reached by further washing, too, but the liquid volumes would mean a problem too big for further processing.

The OTC is precipitated from the acidic filtrate by a calcium salt and a water-soluble silicate, preferably water-glass. If the iron was not precipitated in the first step and then removed, it precipitates now together with the complex salt and remains in this salt. There is a pH-value at which the iron(II) and iron(III) can be separated as silicates but the OTC is not damaged. A pH-value of 4 to 5 is optimal, this is adjusted by a basic substance, suitably by sodium hydroxide.

The rate by which the precipitation reagents are added influences the particle size of the precipitate. Generally a medium particle size is to be obtained since in the case of too small particles the active agent again partly dissolves, and if they are too big, the precipitation is not complete.

As calcium salt calcium chloride is suitably used. As water-soluble silicate practically water glass to be obtained in trade (soda water glass=sodium silicate) is a disposal. It is suitably diluted with water to a fourfold of its volume. 1 to 20 ml, preferably 4 to 9 ml of this dilution related to 1 kg fermentation broth are necessary.

To make the precipitation complete, the pH-value is adjusted to 8 to 11 with 2n sodium hydroxide solution. The mixture is stirred for 30 minutes to 5 hours. The precipitation takes place more rapidly if still a carbonate or hydrogen-carbonate is added. This is probably a salting out effect. Sodium hydrogen-carbonate which is suitably used in a 10 percent solution is the most suitable one. For 1 kg of fermentation broth one takes 0.5 to 10 g, preferably 1 to 3 g of hydrogen carbonate.

Then the precipitated complex is separated from the mother liquor as soon as possible so that the active agent does not dissolve. The correct time is determined by measuring the OTC concentration of the mother liquor, if it has attained a minimum value, filtration is performed. A filter-aid may optionally be used. Under these conditions maximum 0.04 to 0.06 mg/ml of OTC remain in the mother liquor, that is the loss caused by the OTC remaining in the mother liquor is less than 1%.

Then the filter-wet OTC complex salt is dried under atmospheric pressure or in vacuo. The drying temperature is between 20° and 120° C., preferably 100° and 110° C. By constant stirring, separating and turning the drying time is kept as short as possible since the alkaline substance contained in the complex salt (Na, Ca compounds) could attack the active agent.

According to process variant (b) the fermentation broth is directly reacted with the precipitation reagents, that is the calcium salt and the water-soluble silicate. The water-soluble silicate (soda water-glass) is diluted with water in a ratio of 1:1 in this case and used in a quantity of 5–100 ml, preferably about 10 ml, related to 1 kg of fermentation broth.

Water-glass is strongly basic. If the pH-value of 8–11 optimal for the precipitation should not be attained yet, it is adjusted to alkaline by adding a water-soluble base. A carbonate or hydrogen-carbonate may be added for the promotion of the precipitation process. The quantity and the form of the added substance are identical with those given in paragraph (a). The complex salt directly precipitated on the mycelium is separated and dried as described in paragraph (a).

According to the process of the invention an OTC-calcium-silicate complex salt can be prepared in iron fermenters, too, the total iron content mobilizable by diluted acids of which is 2–200 gamma/g. This product is suitable for the preparation of OTC-hydrochloride and OTC-dihydrate. A further advantage of the process according the invention resides in the fact that the yield is higher than with the known processes: about 85% of the OTC contained in the fermentation broth can be obtained. The obtained complex salt contains about 50% of an active agent according to variant (a) and about 18-20% according to variant (b). The product obtained according to variant (b) may be used directly for fodder purposes.

The invention is demonstrated more in detail by means of the following working examples.

EXAMPLE 1

To 2132 g of OTC-fermentation broth (containing totally 15.56 g of OTC) 40 ml of soda water-glass diluted in a ratio of 1:1 (soda water-glass according to Hungarian standard No. MSZ 929, 40°-45° B., and water in a relation of 1:1) are added under stirring at room temperature. Then 150 ml of a 10 percent calcium chloride solution are added and the pH-value is adjusted to 9 by soda water-glass diluted in a ratio of 1:1 of which about 200 ml are necessary. The mixture is stirred for 2 hours, then filtered off. 157.8 g of a dry product are obtained, it contains 14.517 g (9.2%) of pure active agent, this yield corresponds to 93% related to the initial activity.

EXAMPLE 2

45 ml of soda water-glass diluted in a ratio of 1:1 and then 86 ml of 10 percent $CaCl_2$ solution are added to 2076 g of OTC-fermentation broth (containing 16.320 g of OTC) at room temperature. Then the pH-value is adjusted to 9.2 by 2n sodium hydroxide solution and the mixture is reacted with 75 ml of 10 percent sodium hydrogen carbonate solution. The mixture is stirred for 2 hours and filtrated after adding 11 g of perlite. The weight of the dry product is 83.0 g and it contains 15.520 g (18.7%) of OTC what corresponds to a yield of 95%.

EXAMPLE 3

50 ml of soda water-glass diluted in a ratio of 1:1 are added to 2042 g of OTC-fermentation broth (containing totally 19.68 g of OTC) under stirring at room temperature. Then the pH-value is adjusted to 1 by 25 percent sulfuric acid of which about 200 ml are used. The mixture is stirred for 30 minutes, after adding 6 g of perlite, filtrated and the mycelium is washed on the filter with 800 ml of water. Filtrate and wash water are unified. The obtained 2700 ml of liquid contain 17.52 g of OTC. The pH-value is adjusted to 4.5 by 2N sodium hydroxide solution under stirring. The precipitation reagents: 160 ml of 10 percent calcium chloride solution and soda water-glass diluted in a ratio of 1:3 are added. Soda water-glass is used till the pH-value rises to 6.5 (about 29 ml). Then the pH-value is adjusted to 9.2 by 2N sodium hydroxide solution and 50 ml of 10 percent sodium hydrogen carbonate solution are added. 3 hours later filtration and drying are performed. 39.78 g of the product are obtained which contains totally 14.96 g of OTC what corresponds to a yield of 76%.

EXAMPLE 4

153 ml of 10 percent oxalic acid (=90 ml/kg) are added to 1704 g of OTC-fermentation broth (containing totally 16.040 g of OTC) under stirring at room temperature. The pH-value drops to 2. The mixture is filtrated and the mycelium is washed with 426 ml of water (=250 ml/kg). Filtrate and wash water are unified. The obtained 1970 ml of liquid contains 13.794 g of OTC. The pH-value of the solution is adjusted to 4.5 by 2n sodium hydroxide solution. Then 52 ml of 10 percent $CaCl_2$ solution and then until a pH-value of 6.5 water glass diluted in a ratio of 1:3 with water (about 21 ml) are added. After one hour of stirring the pH-value is adjusted to 9 by 2n sodium hydroxide solution. Stirring is continued for three hours, the product is filtrated off and dried. 28.29 g of the product are obtained which contains 13.040 g (46.1%) of OTC, what corresponds to a yield of 81%.

EXAMPLE 5

127 ml of a sulfuric acid/oxalic acid mixture containing 11 percent by weight of sulfuric acid and 1.5 percent by weight of oxalic acid are added to 2124 g of OTC-fermentation broth (containing totally 18.035 g OTC) at room temperature. The pH-value drops to 2. The mixture is stirred for one hour, then perlite is added in a quantity of 5 g/kg and the mixture is filtered. The mycelium is washed by 530 ml of water. The 2390 ml of liquid obtained by unifying the filtrate and the wash water contain 16.646 g of OTC. The pH-value of the solution is adjusted to 4.5 by 2n sodium hydroxide solution. 52.4 ml of water glass diluted in a ratio of 1:3 by water and 160 ml of 10 per cent $CaCl_2$-solution are added to the solution. The pH-value amounting to about 6.5 after this step is adjusted to 9.2 by 2n sodium hydroxiode solution. 51 ml of 10 percent sodium hydrogen carbonate solution are added to the solution. After 2 hours filtration and drying are carried out. 43.69 g of a complex salt containing totally 16.033 g of OTC are obtained. The OTC-yield is 89%.

EXAMPLE 6

From 2109 g of OTC-fermentation broth (containing totally 20.035 g OTC) 2373 ml of filtrate (containing 18.432 g of OTC) are prepared as described in Example 5. The pH-value of the filtrate is adjusted to 4.5 by 2n sodium hydroxide solution (about 88 ml), then after adding 180 ml of 10 percent $CaCl_2$-solution the pH-value is at first adjusted to 6.5 by water-glass diluted in a ratio of 1:3 (about 35 ml are necessary), then to 9.2 by 2n sodium hydroxide solution (about 79 ml). A volume of 10 percent sodium hydrogen carbonate solution (about 35 ml) corresponding to the added volume of water glass is added. After two hours of stirring filtration is performed. The product is dried by hot air (100°-110° C.). 43.6 g of a complex salt are obtained which contains totally 17.43 g of OTC which corresponds to a yield of 87%.

EXAMPLE 7

0.63 g of Sterogenole (cetylpyridiniumbromide) in form of a 10 percent solution prepared with warm water is added to 2065 g of OTC-fermentation broth (containing totally 21.578 g of OTC) under stirring. The pH-value of the mixture is adjusted to 5.3-5.6 by the acid mixture used in Example 5, too. The mixture is heated to 40° C. within 30 minutes and stirrd at this temperature for 2 hours. After cooling to room temperature the pretreated fermentation broth may be further processed according to any of Examples 3 to 6. Depending on the desired purity degree yields of 80 to 90% are obtained.

What we claim is:

1. A process for the preparation of an oxytetracycline-calcium silicate complex salt free from iron impurities from a fermentation broth which contains oxytetracycline, mycelium, and iron impurites which comprises the steps of:
(a) treating the fermentation broth with a water-soluble silicate to cause precipitation of the iron impurities as iron silicates;
(b) acidifying the fermentation broth to a pH of 0.5 to 3.0;
(c) filtering off mycelium and the precipitated iron silicates from the fermentation broth;
(d) adjusting the pH of the fermentation broth treated according to step (c) to 4 to 5 by the addition of lye;
(e) adding a calcium salt and a water-soluble silicate to the fermentation broth and stirring the fermentation broth;
(f) filtering off the mother liquor to yield the desired product; and
(g) drying the desired product at 20° to 120° C.

2. The process defined in claim 1 wherein prior to step (a) the fermentation broth is treated with a surface active agent.

3. The process defined in claim 1 wherein in step (b) a mixture of oxalic acid and sulfuric acid is used for the acidification.

4. The process defined in claim 1 wherein the water-soluble silicate is soda water-glass diluted in a ratio of 1:3 with water in a quantity of 1 to 20 ml related to 1 kg of fermentation broth.

5. The process defined in claim 1 wherein in step (e) the water-soluble silicate is added subsequent to the addition of the calcium salt.

6. The process defined in claim 1 wherein in step (e) the calcium salt is calcium chloride.

7. The process defined in claim 1 wherein step (e), a water-soluble carbonate or bicarbonate is added to the fermentation broth.

8. The process defined in claim 7 wherein sodium bicarbonate is the water-soluble bicarbonate.

9. A process for the preparation of an oxytetracycline-calcium silicate complex salt from a fermentation broth which contains oxytetracycline, which comprise the steps of:
(a) acidifying the fermentation broth to a pH of 0.5 to 3.0;
(b) filtering off mycelium from the fermentation broth;
(c) adjusting the pH of the fermentation broth treated according to steps (a) and (b) to 4 to 5 by the addition of lye;
(d) adding a calcium salt and sodium silicate to the fermentation broth and stirring the fermentation broth;
(e) filtering off mother liquor to yield the desired product; and
(f) drying the product at 20° to 120° C.

10. The process defined in claim 9 wherein prior to step (a) the fermentation broth is treated with a surface active agent.

11. The process defined in claim 9 wherein during step (a) a mixture of oxalic acid and sulfuric acid is used for the acidification.

12. The process defined in claim 9 wherein the sodium silicate is diluted in a ratio of 1:3 with water in a quantity of 1 to 20 ml related to 1 kg of fermentation broth.

13. The process defined in claim 9 wherein in step (d) the sodium silicate is added subsequent to the addition of the calcium salt.

14. The process defined in claim 9 wherein in step (d) the calcium salt is calcium chloride.

15. The process defined in claim 9 wherein in step (d) a water-soluble carbonate or bicarbonate is added to the fermentation broth.

16. The process defined in claim 15 wherein sodium bicarbonate is the water-soluble bicarbonate.

17. A process for the preparation of an oxytetracycline-calcium silicate complex salt from a fermentation broth which contains oxytetracycline, which comprises the following steps:
(a) treating the fermentation broth with a calcium salt and sodium silicate;
(b) stirring the fermentation broth treated according to step (a) to precipitate the oxytetracycline-calcium silicate complex salt;
(c) filtering the oxytetracycline-calcium silicate complex salt; and
(d) drying the oxytetracycline-calcium silicate complex salt at 20° to 120° C.

18. The process defined in claim 17 wherein during step (a) the pH of the fermentation broth is adjusted to 8 to 11.

19. The process defined in claim 17 wherein during step (a) a water-soluble carbonate or bicarbonate is added to the fermentation broth.

20. The process defined in claim 19 wherein the water-soluble bicarbonate is sodium bicarbonate.

21. The process defined in claim 17 wherein the calcium salt is calcium chloride.

* * * * *